(12) United States Patent
Sharpless et al.

(10) Patent No.: US 8,899,833 B2
(45) Date of Patent: Dec. 2, 2014

(54) IMAGING SYSTEM GANTRY

(75) Inventors: Ronald B Sharpless, Cleveland, OH (US); Samuel Andreas Johansson, Cleveland Hts., OH (US); Jeremy D. Pettinato, Parma, OH (US); Joshua S. Sapp, Chardon, OH (US); John Cressman, Chardon, OH (US)

(73) Assignee: Koninklijke Philips N.V., Eindhoven (NL)

( * ) Notice: Subject to any disclaimer, the term of this patent is extended or adjusted under 35 U.S.C. 154(b) by 675 days.

(21) Appl. No.: 13/142,486

(22) PCT Filed: Dec. 9, 2009

(86) PCT No.: PCT/IB2009/055603
§ 371 (c)(1),
(2), (4) Date: Sep. 27, 2011

(87) PCT Pub. No.: WO2010/079392
PCT Pub. Date: Jul. 15, 2010

(65) Prior Publication Data
US 2012/0027183 A1 Feb. 2, 2012

Related U.S. Application Data

(60) Provisional application No. 61/143,447, filed on Jan. 9, 2009, provisional application No. 61/230,856, filed on Aug. 3, 2009.

(51) Int. Cl.
*H05G 1/02* (2006.01)
*F16C 19/16* (2006.01)
*A61B 6/03* (2006.01)

(52) U.S. Cl.
CPC .............. *F16C 19/163* (2013.01); *A61B 6/035* (2013.01); *F16C 2300/14* (2013.01); *F16C 2316/10* (2013.01)

USPC .......................................... 378/197

(58) Field of Classification Search
CPC ...... A61B 6/0306; A61B 6/56; A61B 6/4441; A61B 6/4464
USPC ...................... 378/15, 17, 195, 197
See application file for complete search history.

(56) References Cited

U.S. PATENT DOCUMENTS

| 4,115,695 A | 9/1978 | Kelman |
| 4,736,075 A | 4/1988 | Amor et al. |

(Continued)

FOREIGN PATENT DOCUMENTS

| JP | H09238931 A | 9/1997 |
| JP | 2005517975 A | 6/2005 |

(Continued)

OTHER PUBLICATIONS

Newway Air Bearings; Radial Air Bearing Product Line Launch Press Release; Rev. 3; Tuesday, Apr. 14, 2009 http://www.newwayairbearings.com/Computed-Tomography.

*Primary Examiner* — Irakli Kiknadze

(57) ABSTRACT

An imaging system (100) includes a rotating frame (106), a second frame (102, 104), and a support (108) that rotatably couples the rotating frame (106) to the second frame (102, 104). One of the rotating frame (106) or the second frame (102, 104) is compliantly coupled to the support (108) and the other of the rotating frame (106) or the second frame (102, 104) is rigidly coupled to the support (108). An imaging system includes a rotating frame (106), a tilt frame (104), and a stationary frame (102). A frame stiffener (110) provides structural support for the rotating and tilt frames (106, 104) along transverse axes. An imaging system (100) includes a rotating frame (106) and a second frame (102, 104) that rotatably supports the rotating frame (106). The rotating frame (106) is coupled to the second frame (102, 104) through a contactless bearing and controlled by a contactless mechanism. A braking component (112) selectively applies a brake to the rotating frame (106).

28 Claims, 12 Drawing Sheets

(56) References Cited

U.S. PATENT DOCUMENTS

| | | |
|---|---|---|
| 5,799,054 A | 8/1998 | Hum et al. |
| 6,276,145 B1 | 8/2001 | Sharpless et al. |
| 6,337,894 B1 | 1/2002 | Tybinkowski et al. |
| 6,382,336 B1 | 5/2002 | Smith |
| 6,404,845 B1 | 6/2002 | Sharpless et al. |
| 6,428,206 B1 | 8/2002 | Watanabe |
| 6,590,953 B2 * | 7/2003 | Suzuki et al. .......... 378/15 |
| 6,614,871 B1 | 9/2003 | Kobiki et al. |
| 6,721,388 B2 * | 4/2004 | Tybinkowski et al. ...... 378/17 |
| 7,020,233 B1 | 3/2006 | Tybinkowski et al. |
| 7,023,952 B2 | 4/2006 | Brunnett |
| 7,390,127 B2 | 6/2008 | Kono et al. |
| 7,396,089 B2 | 7/2008 | Bennett et al. |
| 7,477,721 B2 | 1/2009 | Chappo et al. |
| 2004/0062343 A1 | 4/2004 | Brunnett et al. |
| 2005/0063709 A1 | 3/2005 | Poisel et al. |
| 2007/0274436 A1 | 11/2007 | Harada et al. |

FOREIGN PATENT DOCUMENTS

| | | |
|---|---|---|
| WO | 0053936 A1 | 9/2000 |
| WO | 03069392 A2 | 8/2003 |

* cited by examiner

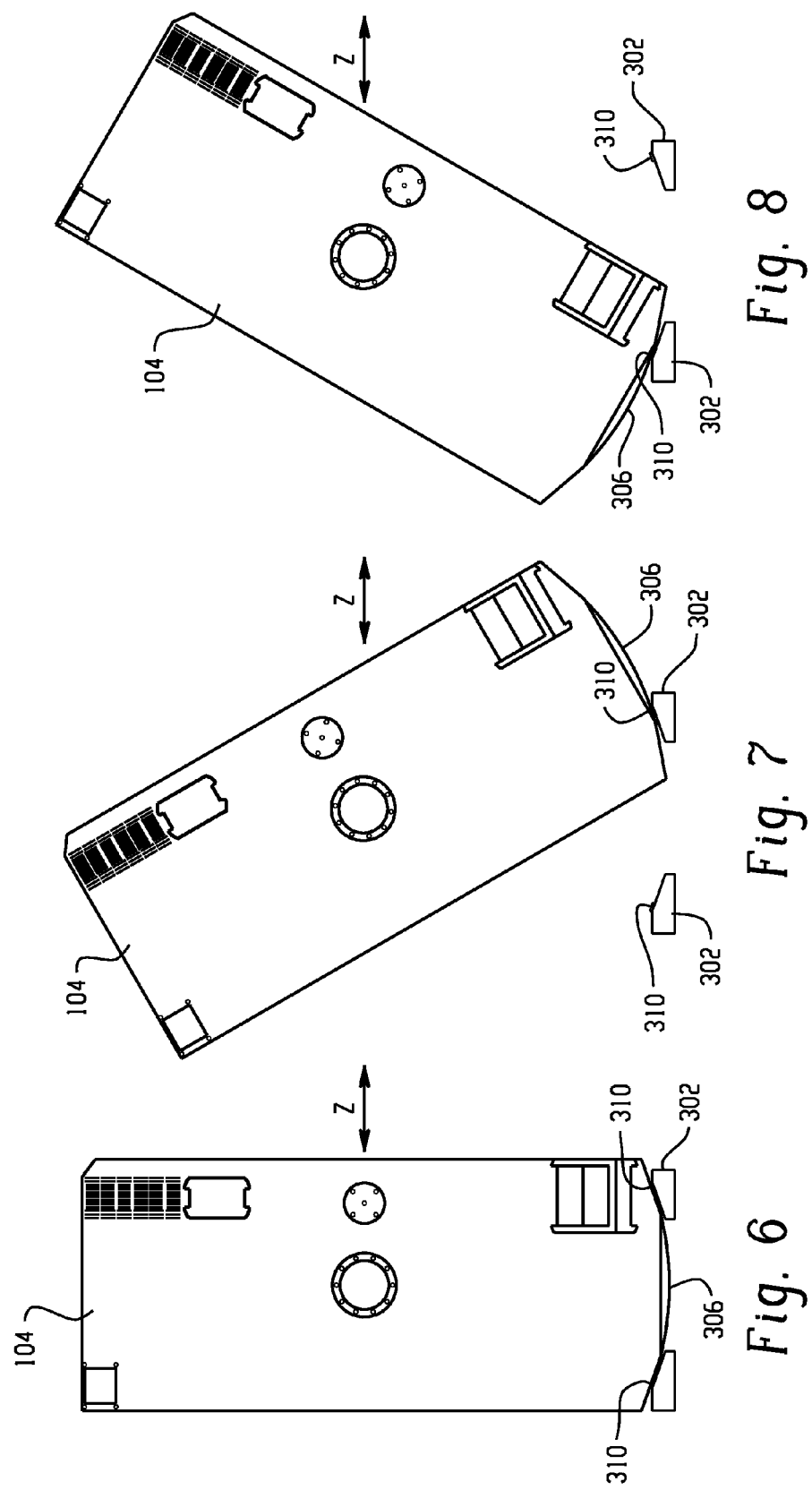

IMAGING SYSTEM GANTRY

CROSS REFERENCE TO RELATED APPLICATIONS

This application claims the benefit of U.S. provisional application Ser. No. 61/143,447 filed Jan. 9, 2009 and U.S. provisional application No. 61/230,856 filed Aug. 3, 2009, which is incorporated herein by reference.

The following relates to imaging systems and finds particular application with computed tomography (CT) imaging. However, it is also amenable to other medical imaging and non-medical imaging applications.

A computed tomography (CT) scanner generally includes an x-ray tube and a detector array that detects radiation emitted from the x-ray tube. The x-ray tube and detector array are mounted on a rotating frame that rotates around an examination region about a z-axis. The rotating frame is rotatably supported by a tilting frame via a bearing or the like. The tilting frame is supported by a stationary frame, and tilts about an x-axis along the z-axis. The stationary frame mounts to the floor in an examination room.

Unfortunately, various forces acting on the rotating frame (e.g., gravitational, radial, etc.) tend to cause stresses that may decrease the lifetime and performance of various components, such as the bearing used to couple the rotating frame to the tilting frame. In addition, a relatively flexible bearing is often coupled to relatively stiff rotating and tilting frames. As a result, raceway distortion may occur, which can introduce raceway stress when rotating the rotating frame. The amount of such stress generally is proportional to the deformation and mounted stiffness. Furthermore, the mounting surface may vary in accuracy from scanner to scanner, which can lead to a wide variance in performance of the bearing.

The various forces acting on the rotating frame, as well as vibration, also tend to cause rotating frame imbalances. Such imbalances can cause the rotating frame to wobble, which may vary the center of the field of view during a scan, which can degrade image quality. The degree of wobble is based on various factors such as the rotational speed of the rotating frame, the stiffness of the supporting structure, etc. The stiffness of scanners configured to tilt tends to be less due to the available locations at which the stationary frame can be affixed to the floor in the examination room, which may lead to increase wobble.

When power becomes unavailable while the rotating frame rotates, it generally is desirable to controllably stop the rotating gantry from rotating. Traditional systems had a friction brake on the motor and relatively high rotational friction, which would slow the rotating frame to a complete stop when power was lost. More recent scanner have increased rotational speeds, lower friction bearings and contactless rotor motion systems, which have led to increased deceleration times when power is lost. Unfortunately, friction braking of the motor is not available when the motor is non-contacting. In addition, with a lower friction bearing, the coast down times can be excessively long if only wind power (air friction) is used to slow the rotating frame to a complete stop.

Aspects herein address the above-referenced matters and/or others.

According to one aspect, an imaging system includes a rotating frame that rotates around an examination region about a z-axis, a second frame, and a support that rotatably couples the rotating frame to the second frame. One of the rotating frame or the second frame is compliantly coupled to the support and the other of the rotating frame or the second frame is rigidly coupled to the support.

According to another aspect, an imaging system includes a rotating frame that rotates around an examination region about a z-axis, a tilt frame that tilts along the z-axis, wherein the rotating frame is rotatably coupled to the tilt frame, and a stationary frame, wherein the tilt frame is tiltably coupled to the stationary frame. A frame stiffener provides structural support for the rotating and tilt frames along transverse axes.

According to another aspect, an imaging system includes a rotating frame that rotates around an examination region about a z-axis and a second frame that rotatably supports the rotating frame. The rotating frame is coupled to the second frame through a contactless bearing and controlled by a contactless mechanism. A braking component selectively applies a brake to the rotating frame.

According to another aspect, a system includes a rotating gantry that rotates around an examination region about a z-axis and a stationary gantry. A contactless fluid bearing rotably couples the rotating gantry and the stationary gantry. The contactless bearing includes a first portion affixed to the rotating gantry and a second portion affixed to the stationary gantry. The second portion engages the first portion to brake the rotating gantry.

According to another aspect, a method includes rotatably coupling a rotating frame of an imaging system and a second frame of the imaging system. One of the rotating frame or the second frame of the imaging system is compliantly coupled to a support of the imaging system and the other of the rotating frame or the second frame of the imaging system is rigidly coupled to the support of the imaging system.

According to another aspect, a method includes providing lateral support for rotating and tilt frames of an imaging system via a frame stiffener. Tilt frame is tiltably coupled to a stationary frame of the imaging system (100) and tilts along a z-axis and the rotating frame is rotatably coupled to the tilt frame and rotates about the z-axis. According to another aspect, a method includes employing a first portion of a contactless bearing of an imaging system to brake a rotating second portion of the contactless bearing and hence a rotating gantry coupled to the second portion. The contactless bearing couples a rotating gantry of the imaging system to a stationary gantry of the imaging system.

The invention may take form in various components and arrangements of components, and in various steps and arrangements of steps. The drawings are only for purposes of illustrating the preferred embodiments and are not to be construed as limiting the invention.

FIGS. 3-8 illustrate an example gantry stiffener.

Figure 1:
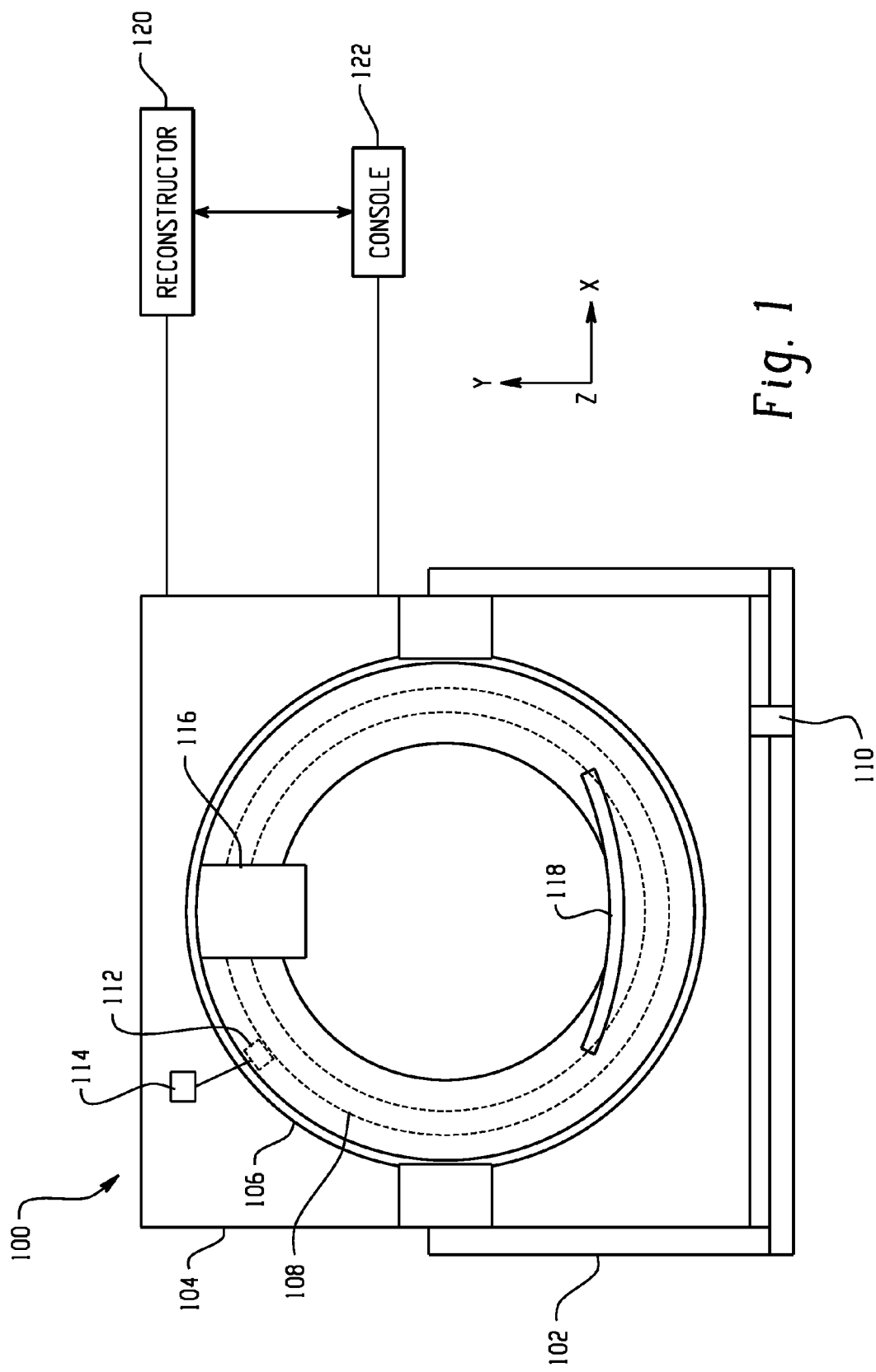
FIG. 1 illustrates an imaging system.

FIG. 1 illustrates a scanner or imaging system 100 that includes a stationary frame 102, a tilt frame 104, and a rotating frame 106. The stationary frame 102 mounts to the floor in an examination room. The tilt frame 104 is tiltably mounted to the stationary frame 102 and is configured to tilt about an x-axis along the z-axis. In one embodiment, the tilt frame 104 is configured to tilt up to thirty (30) degrees in both directions along the z-axis. The rotating frame 106 is rotatably supported by the tilt frame 104 via a support 108, which includes a bearing such as a ball bearing, an air bearing, a magnetic bearing, etc. The rotating frame 106 rotates around an examination region about the z-axis. In some embodiments, the tilt frame 104 is omitted and the rotating frame 106 is rotatably supported by the stationary frame 102.

As described in greater detail below, in one non-limiting embodiment the support 108 includes a stator portion and a bearing portion, which is coupled to the stator portion via a compliant bearing support. The compliant bearing support allows one side of support to be generally compliant with respect to the other side of the support, which is generally more rigid. For example, the bearing portion may form the generally more compliant side and the stator portion may form the generally more rigid side, or vice versa. Such a compliant bearing support may provide global stiffness while relieving localized operating stresses on the bearing.

Also described in greater detail below, in one non-limiting embodiment the system 100 includes at least one stiffener 110 that can reduce motion along the x and y-axis directions relative to a configuration in which the stiffener 110 is omitted. This includes reducing such motion when the tilt frame 104 is in a non-tilt vertical position or a tilt position.

Further described in greater detail below, in one non-limiting embodiment a braking component 112 is used to slow down and/or stop the rotating frame 106 from rotating around the z-axis. A controller 114 controls the braking component 112. The braking component 112 allows for braking during normal and/or errant operating conditions. By way of example, when the system 100 is configured with an air bearing and system power is lost, the braking component 112 can be used to ramp down and stop a relatively frictionless bearing from rotating.

A radiation source 116, such as an x-ray tube, is coupled to and rotates with the rotating frame 106 around the examination region. The radiation source 116 emits radiation that traverses the examination region. A detector array 118 subtends an angular arc, across from the radiation source 116, opposite the examination region. The detector array 118 includes one or more rows of radiation sensitive pixels that extend along the transverse direction. The radiation sensitive pixels detect radiation traversing the examination region and respectively generate a signal indicative thereof.

A reconstructor 120 reconstructs the signals and generates volumetric image data indicative of the examination region. A patient support (not shown), such as a couch, supports a patient in the examination region. The patient support is movable along an x, y and/or z-axis. A general purpose computing system serves as an operator console 122, which includes input and human readable output devices such as a keyboard and/or mouse and a display and/or printer. Software resident on the computing system controls operation of the system 100.

Figure 2:
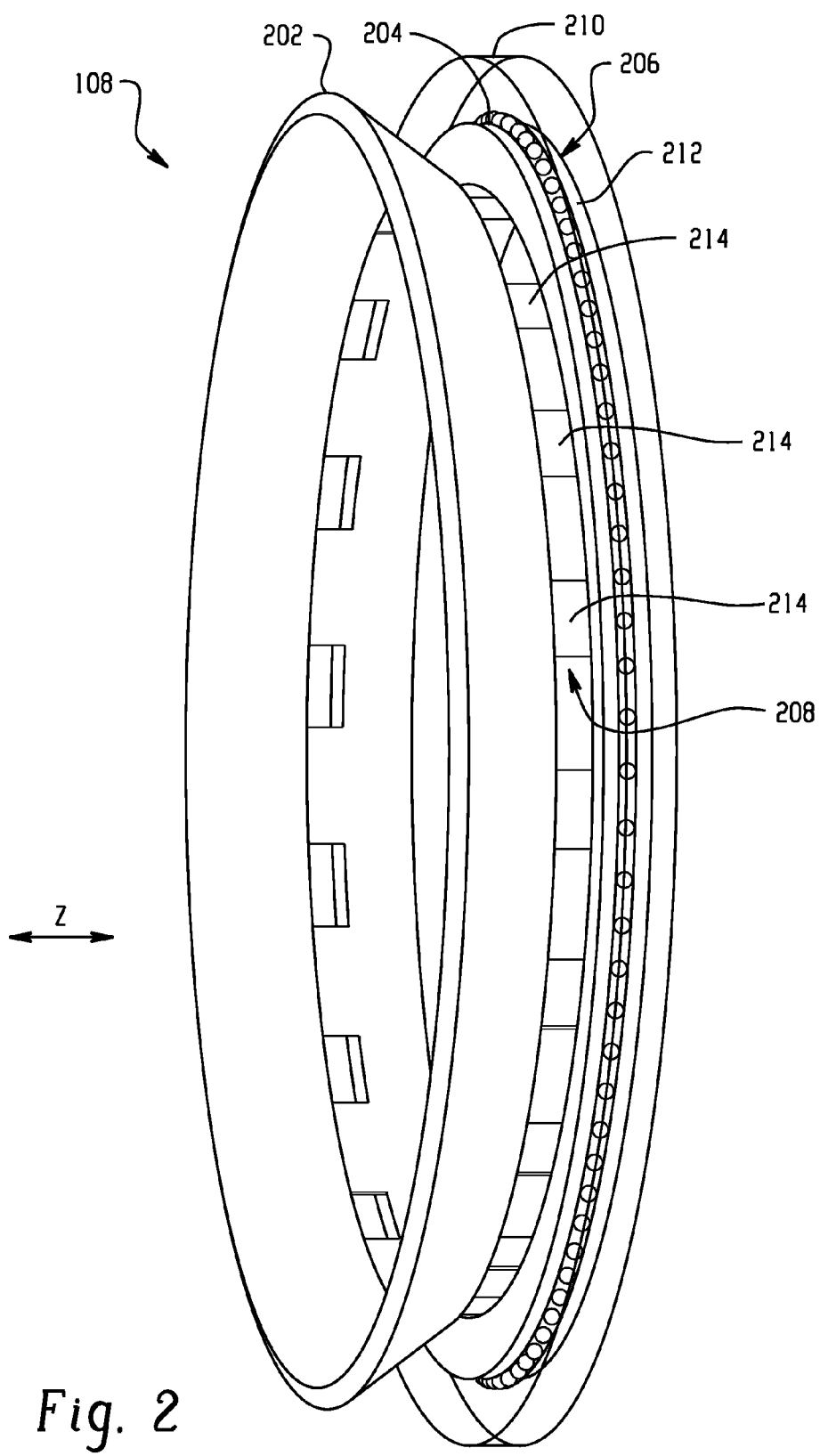
FIG. 2 illustrates an example bearing support.

As briefly discussed above, in one non-limiting embodiment the support 108 includes a stator portion and a bearing portion, which is coupled to the stator portion via a compliant bearing support. FIG. 2 illustrates a non-limiting example of such a support.

In this example, the support 108 includes a stator 202, a first portion 204 of a bearing 206 and a bearing support 208 disposed therebetween. The bearing support 208 couples the stator 202 and the first portion 204 of the bearing 206. The first portion 204 of the bearing 206 is compliantly coupled to the bearing support 208. A rotor 210 is affixed to a second portion 212 of the bearing 206. The rotor 210 is rotatably coupled to the stator 202 via the bearing 206. The stator 202 is rigidly affixed to the tilt frame 104 and provides relatively rigid global support for the rotor 210.

In the illustrated embodiment, the bearing support 208 includes a plurality of members or flexures 214. As shown the flexures 214 are spaced apart from each other with a material free region therebetween. In this example, at least one of the flexures 214 is an individual member affixed to the stator 202 and the bearing 206. Such a flexure 214 can be affixed via a screw, a bolt, a rivet, an adhesive, and/or other suitable fastening mechanism. In another embodiment, two or more of the flexures 214 are part of a single member affixed to the stator 202 and the bearing 206. In yet another embodiment, at least one of the flexures 214 is part of the stator 202, the bearing 206, or both the stator 202 and bearing 206. A flexure 214 can be formed from a metal, a plastic, or other suitable material.

The flexures 214 allow for localized compliance at the bearing 206. In one instance, a subset (e.g., one or more) of the flexure 214 may bend, shear, compress, stretch and/or otherwise physically deform based on the coupling between the first and second portions 204, 212 of the bearing 206, loads, forces, and/or otherwise. Such deformation generally is based on the geometrical imperfections of the bearing 206, rotor loading, gravitational forces, other forces, etc. and may reduce localized operating stresses relative to a configuration in which the bearing support 208 is more rigid or stiff. This may increase the lifetime of the bearing 206 and allows for a bearing with less stringent tolerances, which may reduce overall system cost.

By way of example, the raceways and balls of the bearing 206 generally are relatively rigid structures that are machined within a pre-determined tolerance and based on the technical limitations of the tooling. As such, the geometry of the raceways and the balls is less than perfect. In addition, rotor loads can cause raceway distortions, and bearing mounting surfaces introduce a degree of inaccuracy. The imperfect geometry, distortions and inaccuracies introduce varying localized operating stresses. Generally, the amount of stress is proportional to the degree of rigidity or stiffness. The flexures 214 are compliant and can deform and, thus, reduce such operating stresses. As noted above, the rigid coupling between the stator 202 and the tilt frame 104 provides global stiffness for the rotating frame 106.

Of course, the dimensions of the flexures 214 and/or the material free regions in the illustrated example are provided for explanatory purposes. In other embodiments, other dimensions are contemplated.

As briefly discussed above, in one non-limiting embodiment the stiffener 110 is employed with the system 100. FIGS. 3-8 illustrate an example gantry stiffener 110.

Figure 3:
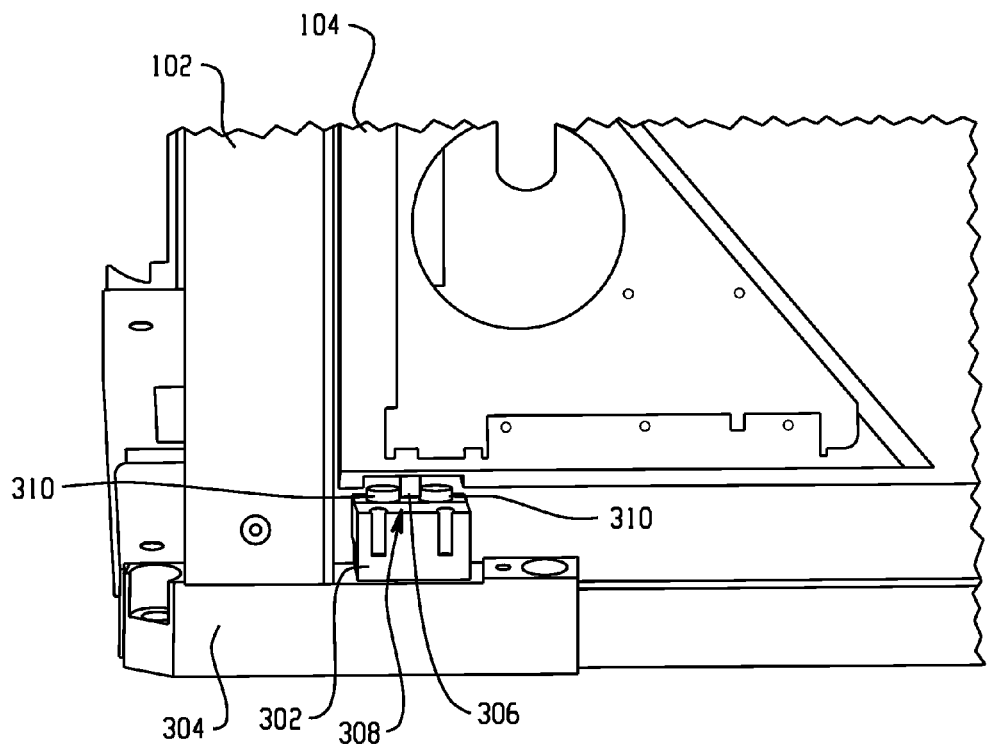
Figure 4:
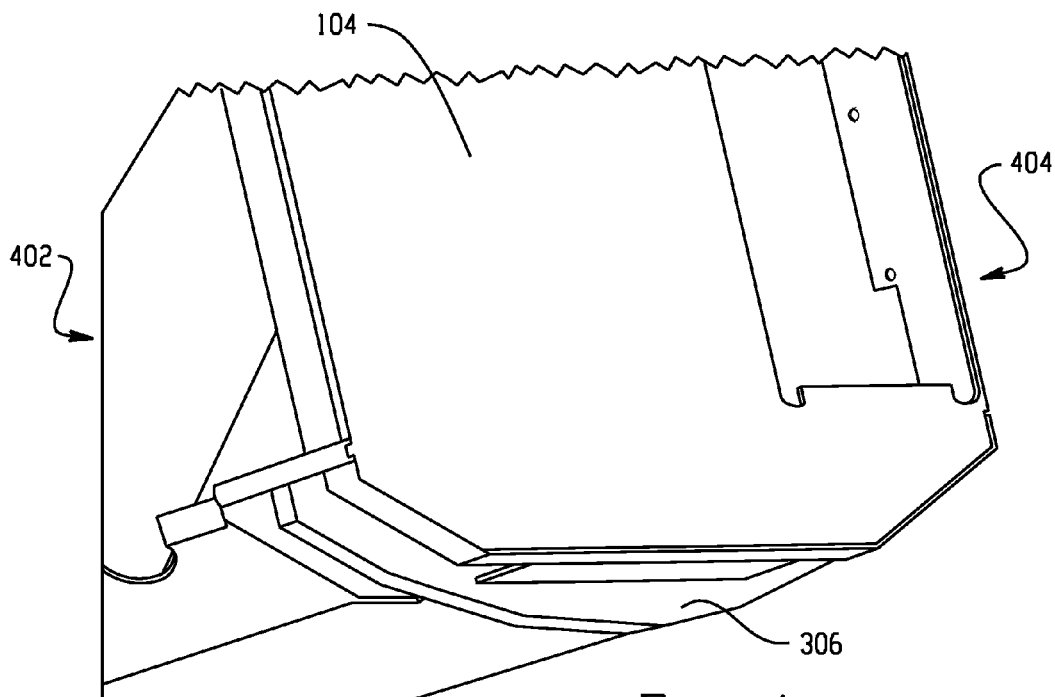

Initially referring to FIG. 3, the gantry stiffener 110 includes a first portion 302 that affixes to a base 304 of the stationary frame 102 and a protruding portion 306 that protrudes from the tilt frame 104 along the y-axis towards the base 304. The first portion 302 affixes to the base via fasteners such as screws, bolts, rivets or the like and includes at least two guides 310 that form a recess or channel 308 in which the protruding portion 306 slides within. As shown in FIG. 4, the protruding portion 306 extends along the z-axis from a front portion 402 of the tilt frame 104 to a rear portion 404 of the tilt frame 104.

Figure 5:
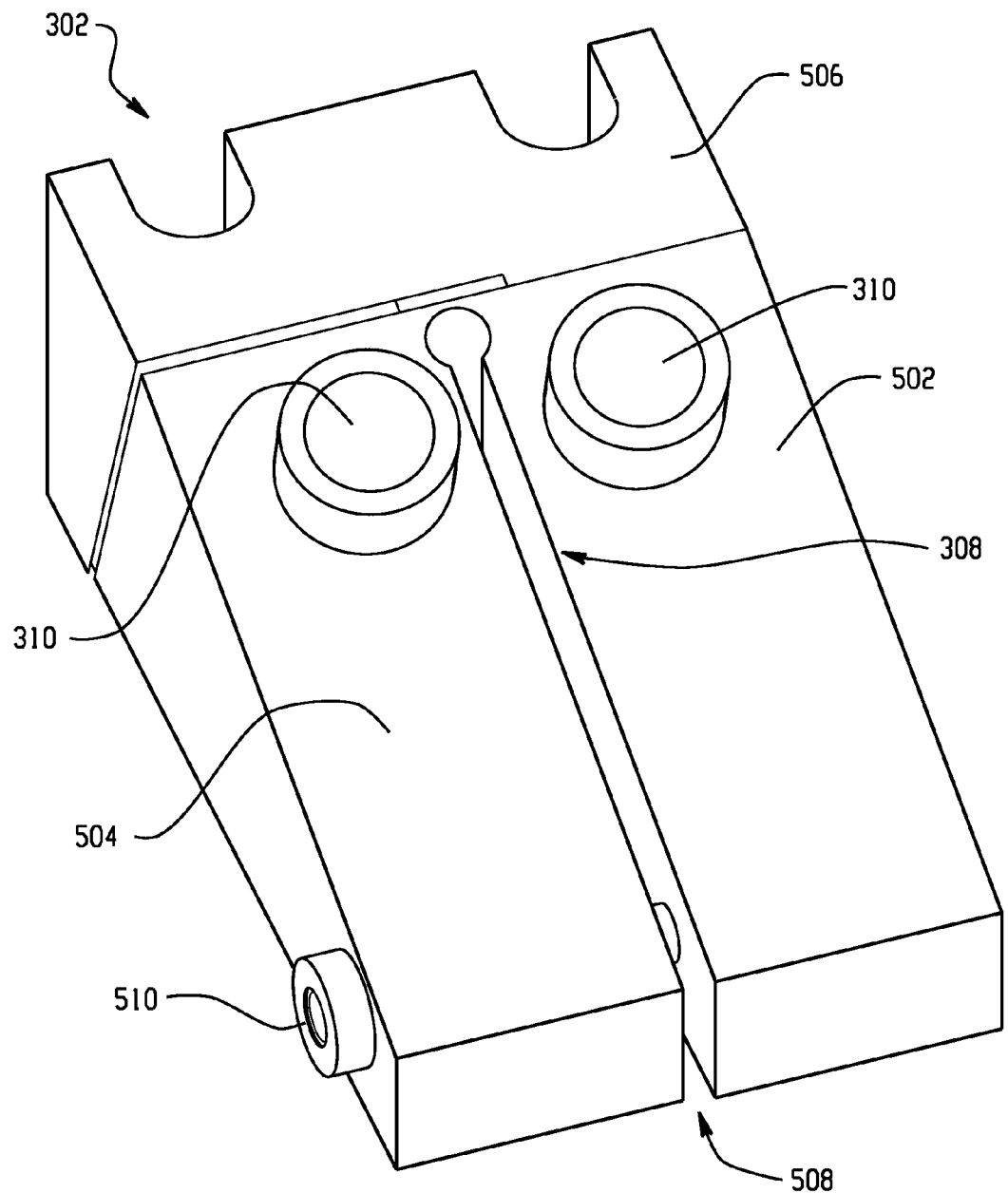

FIG. 5 illustrates an example of the first portion 302 of the gantry stiffener 110. The illustrated first portion 302 includes a generally stationary region 502, which stationarily mounts to the base 304, and a free floating region 504. The stationary and free floating regions 502, 504 are a separated from each other via a material free region 508 and come together at a base region 506. A fastener 510 extends through the free floating region 504 and fastens to the stationary region 502.

The fastener 510 may include a spring or other component that allows the fastener 510 to be fastened with a predetermined preload. The preload can be determined based on the application and/or otherwise. In one instance, such preloading is achieved via a spring or the like. For example, the fastener 510 may be a screw with a spring, where tightening the screw compresses the spring, thereby loading the spring.

In one instance, the preload urges the free floating region 504 towards the stationary region 502, but allows the free floating region 504 to flex or move away from the stationary region 502 when a force having a greater magnitude than the preload is applied to the free floating region 504 in a direction away from the stationary region 502. As such, when the protruding portion 306 on the tilt frame 104 is between the guides 310, the free floating portion 504 is urged against the protruding portion 306, which facilitates reducing motion (e.g., due to rotating frame wobble) of the protruding portion 306 and, hence, the tilt and rotating frames 104,106 along the x and y-axes.

In one instance, the preload is such that both the stationary portion 502 and the free floating portion 504 are always in contact for worst case rotor imbalance. In this instance, the free floating portion 504 moves away or towards the stationary portion 502 dependent on a local thickness of the protruding portion 306. This allows the tilt frame 104 to freely move laterally on the tilt support to compensate for surface flatness and perpendicularity errors of the protruding portion 306 and/or the stationary portion relative to the tilt axis.

FIGS. 6-8 show side views of a portion of the system 100, including the tilt frame 104 and the stiffener 110. As shown, in one embodiment at least two gantry stiffeners 110 are employed, one on each side of the system along the z-axis. FIG. 6 shows the tilt frame 104 in a vertical position. At this position, the protruding portion 306 lies within the guides 310 of both of the gantry stiffeners 110.

In FIG. 7, the tilt frame 104 is tilted in a first direction along the z-axis. As the tilt frame 104 moves from the vertical position (FIG. 6) to this illustrated position, the protruding portion 306 slides through the guides 310, continuously sliding through a first of the two guides 310 while eventually leaving a second of the two guides 310. FIG. 8 shows the tilt frame 104 tilted in an opposite direction along the z-axis. Using two guides 310, as shown, allows at least one guide 310 to provide additional lateral support at all times.

It is to be understood that in another embodiment a single guide 310 is used. In another embodiment, more than one stiffener 110 can be used. Suitable locations for the stiffener 110 includes nearer one of the sides of the stationary frame 102, at about a center region of the tilt frame 104, and/or otherwise. It is also to be understood that rollers could be used to drive the tilt.

Figure 11:
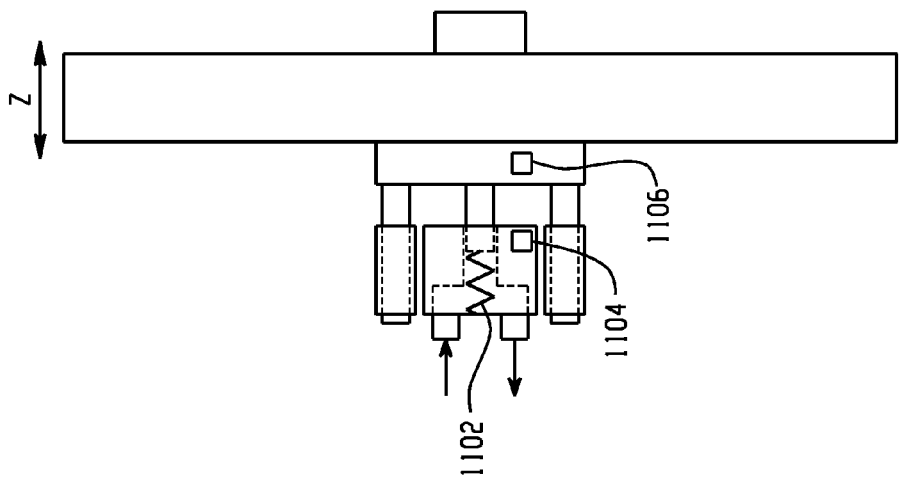
FIGS. 9-11 illustrate an example braking component.
Figure 10:
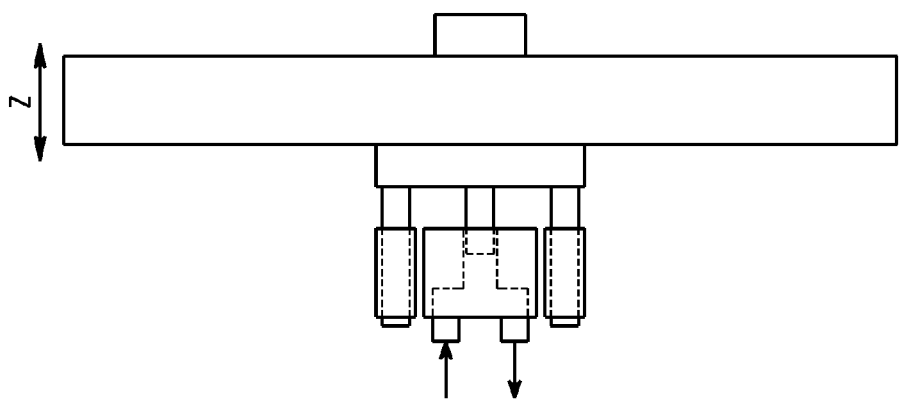
Figure 9:
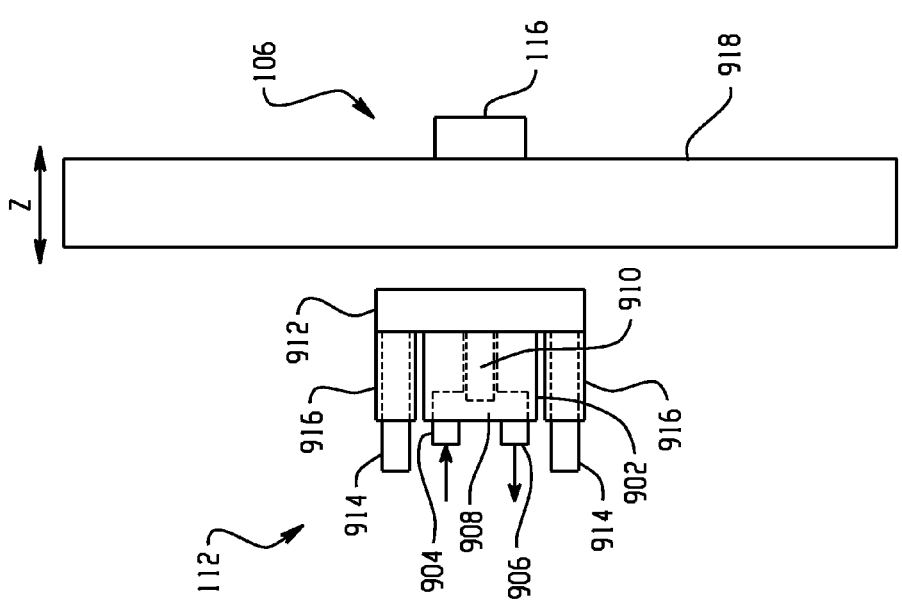

As briefly discussed above, in one non-limiting embodiment the braking component 112 is employed with the system 100. FIGS. 9-11 illustrate an example braking component 112 in connection with the rotating gantry 106, looking down at the system towards the floor. In this example, the braking component 112 is located at the twelve O'clock position for explanatory purposes. However, it is to be understood that the braking component 112 can be variously located. In addition, more than one braking component 112 can be used.

Initially referring to FIGS. 9 and 10, the braking component 112 includes an actuator 902. The illustrated actuator 902 includes an inlet or first port 904, an outlet or second port 906, a chamber 908 and a rod 910 such as a piston or the like. The rod 910 is configured to translate between a first retracted position (FIG. 9) in the chamber 908 and a second extended position (FIG. 10) in the chamber 908.

Gas such as air, a fluid, water, etc. entering the inlet port 904 fills the chamber 908, urging the rod 910 to move into the second extended position. The incoming medium may also be used to apply a load when a force is exerted on the rod 910 in the direction of the first retracted position. The air may be provided to the inlet port 904 via a pressurized reservoir, a tank, a compressor, a pump or the like. Releasing the gas via the outlet port 906 allows the rod 910 to move to the first retracted position. Suction or the like may be used to remove the fluid and pull the rod 910 to the first retracted position.

A brake shoe 912 is affixed to an end of the rod 910 that extends out of the chamber 908 and actuator 902 when the rod 910 is in the second extended position. As such, the brake shoe 912 also moves between a first retracted position (FIG. 9), and a second extended position (FIG. 10) at which the brake shoe 912 is in physical contact with a rotor 918 of the rotating frame 106. In one instance, the brake shoe 912 includes a metal housing to which a friction material or pad is bonded. The housing is affixed to the rod 910 and supports and dissipates heat away from the friction material. The friction material has a suitable coefficient of friction for the system in which it is affixed.

One or more additional rods 914 are also affixed to the brake shoe 912 and translate within corresponding guides 916. As such, the rods 914 translate within the guides 916 between first retracted positions (FIG. 9) and second extended positions (FIG. 10) with the brake shoe 912. The rods 914 can be used to facilitate aligning the brake shoe 912 and carrying system shear loads. In one instance, the rods 914 include steel and translate along ball or other bearings of the guides 916. Such bearings may serve to provide smooth operation, resistant to jamming, as well as to prevent shear loads from damaging the actuator 902.

In one embodiment, the actuator 902 automatically actuates the brake shoe 912 when system power is lost. In this embodiment, when power is available, the actuator 902, via a solenoid or the like, automatically closes the inlet port 904 and opens the outlet port 906. With this embodiment, electrical power is provided to the actuator 902, which maintains the above states of the ports 904, 906. When power is lost, power is removed from the actuator 902, and the actuator 902 automatically opens the inlet port 904 and closes the outlet port 906, which allows the fluid to enter the chamber 908, urging the rod 910 forward to engage the rotor 918.

Friction between the brake shoe 912 and the rotor 918 causes the rotating frame 106 to slow down and stop rotating. When power is restored, the actuator 902 automatically opens the inlet port 904 and closes the outlet port 906, releasing the brake shoe 912. In this embodiment, fluid leaving the chamber 908 pulls the rod 910 and hence the brake shoe 912 away from the rotor 918. This embodiment allows the brake shoe 912 to engage and stop the rotor 918 automatically upon loss of power. Otherwise, the brake shoe 912 does not engage the rotator 918, and the rotor 918 is free to rotate.

FIG. 11 shows an embodiment in which a return spring 1102 is affixed to the rod 910 under tension. When power is lost, the fluid entering the inlet port 904 overcomes the tension force and the brake shoe 912 is urged forward to engage the rotor 918. When power is available, the return spring 1102 maintains the rod 910 in the retracted position or pulls the rod 910 from the second extended position to the first retracted position and hence the brake shoe 912 away from the rotor 918. In this embodiment, suction may or may not be used to pull the rod 910 to the first retracted position.

In another embodiment, the controller 114 generates a control signal that invokes the actuator 902 to extend the brake shoe 912 to brake the rotor 918. With this embodiment, the brake shoe 912 can be used to also selectively brake the rotor 918 when power is available, for example, during any or all braking cycles. This may include solely braking the rotor 918 using the braking component 112 or using the braking component 112 to assist other braking techniques.

In another embodiment, a sensor 1104 and/or 1106 (FIG. 11) is affixed to the braking component 112 and senses whether the brake shoe 912 is engaged with the rotor 918 or not. This information can be used to prevent the system 100 from trying to rotate the rotating frame 106 when the brake is engaged. Such a sensor can be integrated into the solenoid or integrated into the actuator 902. The sensor may alternatively be a displacement sensor, which senses motion of the rod 910 and/or the brake shoe 912.

Although the embodiments above are described in connection with a CT scanner, it is to be appreciated that other imaging and/or non-imaging application are contemplated herein. For example, bearing concept described at least in connection with FIGS. 1 and 2 can be applied to any bearing, including, but not limited to, large diameter bearings with relatively low stiffness and/or thin cross-section. Such bearings can be found in tank turrets, excavators, helicopter and windmills to name a few. In some instance, the bearing may be referred to as a slew-bearing. Of course, the concept can also be applied to small and/or medium sized bearings.

Large diameter thin cross-sections bearings generally are more susceptible to raceway distortions as compared to smaller ones, due to their inherently relatively lower stiffness, thus making them more compliant as compared to its smaller counter parts. Since bearings generally are relatively flexible/compliant they will generally assume/take the stiffness of their supporting structure/housing. If the supporting structure is non-uniform in its stiffness (or load transmitting paths) then the stiffer parts will be seen as structural hard-points. At these hard points excessive bearing loads may be seen, this reduces bearing life. By way of example, for a large bearing/ring (30 ft in diameter) suspended in air by three supporting pillars, at each of the pillars there would be a structural hard point.

More generally, applications other than bearings are also contemplated. An example would be anytime there is a need to join two critical surfaces together (axially or radially). In such instance, the flexures would deform and leave the surfaces/features intact. For example, the shape of the features would stay the same, however the flexures conform fully to the non-perfect surfaces.

Figure 13:
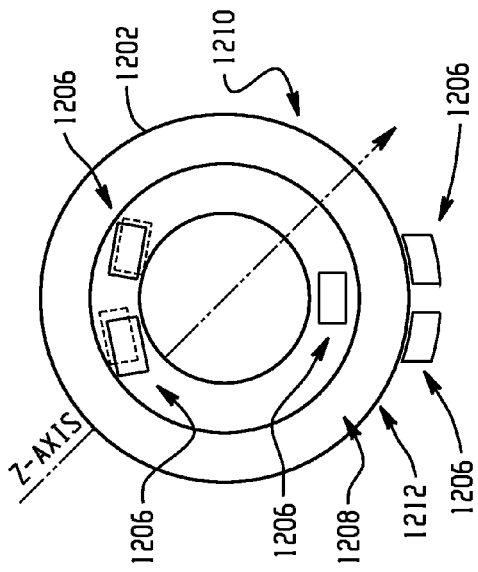
FIGS. 12-14 illustrate an example contactless bearing.
Figure 14:
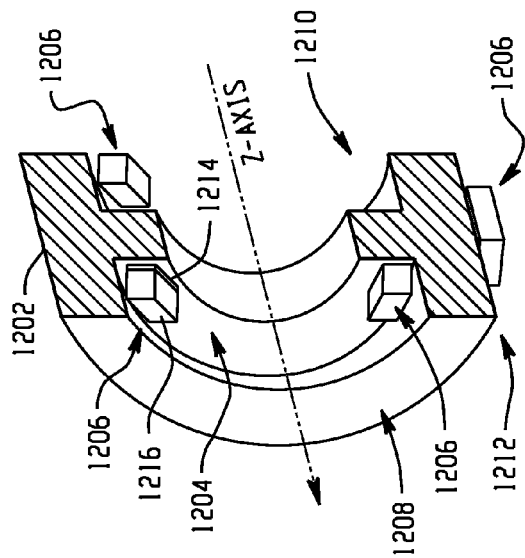
Figure 12:
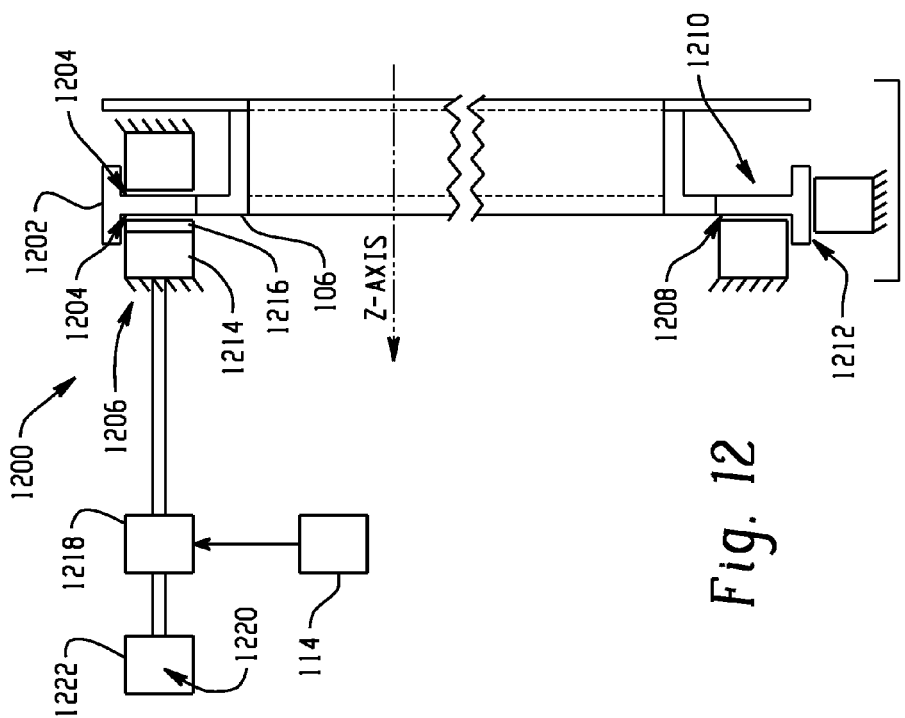

FIGS. 12, 13 and 14 illustrate an embodiment in which the system 100 includes a contactless bearing 1200 such as an air bearing and the braking component 112 (FIG. 1) is part of the contactless bearing 1200. FIG. 12 shows a cross-sectional view of the air bearing 1200 from the side, FIG. 13 shows a view of the air bearing 1200 from a back of the system 100, and FIG. 14 shows a perspective view of the air bearing 1200.

Examples of suitable air bearings are described in U.S. Pat. Nos. 6,276,145, 6,404,845, and 7,023,952, and patent application Ser. No. 11/568,227, the entirety of which are incorporated herein by reference. The air bearing 120 can be driven with a non-contacting motor such as an induction motor, a DC brushless motor, a magnetic motor, or other non-contacting motor.

With respect to FIGS. 12-14, the bearing 1200 includes a first portion 1202, which is affixed to the rotating gantry 106. The first portion 1202 rotates with the rotating gantry 106. The illustrated first portion 1202 is an annular "T"-shaped ring with a bearing race 1204 on each side of the "T." Other shapes for the first portion 1202 are also contemplated herein.

With further respect to FIGS. 12-14, the bearing 1200 also includes one or more second portions 1206, which are affixed to the stationary gantry 102 (not visible). The second portions 1206 are located adjacent to the bearing race 1204. As described in greater detail below, a fluid is used to separate the second portions 1206 from the bearing race 1204, thereby allowing the rotating gantry 106 to freely rotate.

Note that in FIGS. 12-14, there are a total of seven (7) second portions 1206, three (3) located on a back side 1208 of the "T," two (2) located on a front side 1210 of the "T," and two (2) located adjacent to an outside perimeter 1212 of the "T." Other embodiments include more or less second portions 1206, including differently located second portions 1206.

In the illustrated embodiment, a valve 1218 such as a solenoid selectively allows fluid 1220 (e.g., air) from a fluid source 1222 to flow to the second portion 1206 to facilitate creating a substantially frictionless fluid gap between the second portion 1206 and the race 1204. The fluid provided to the valve 1218 can come from various sources such as a pressurized chamber, a compressor, a fluid air mover, or the like. For sake of clarity and brevity, only one valve 1218 is shown in the illustrated example. However, a valve 1218 can be used with two or more of the second portions 1206, including all of the second portions 1206.

The controller 114 (FIG. 1) controls the valve 1218. In one instance, the valve 1218 is an electrically controlled normally open valve and is closed via a control signal from the controller 114. In this instance, without the control signal, the valve 1218 automatically opens and fluid is inhibited from flowing through the valve 1218. A spring-loaded valve can be used to facilitate opening the valve 1218 or transitioning the valve 1218 from a closed state to an open state. The controller 114 can also generate a control signal that controllably opens the valve 1218 or not supply the control signal to controllably open the valve 1218. In other embodiments, a normally closed or other valve is employed.

In the illustrated embodiment, at least one of the second portions 1206 includes a bearing block 1214 with a brake pad 1216 attached thereto and is configured to move between a first position in which the brake pad 1216 physically engages the race 1204 and a second position in which the brake pad 1216 is separated from the race 1204. When engaging the race 1204, the brake pad 1216 inhibits the rotating gantry 106 from rotating or slows down the rotating gantry 106. When disengaged or separated from the race 1204, the rotating gantry 106 can freely rotate.

Figure 15:
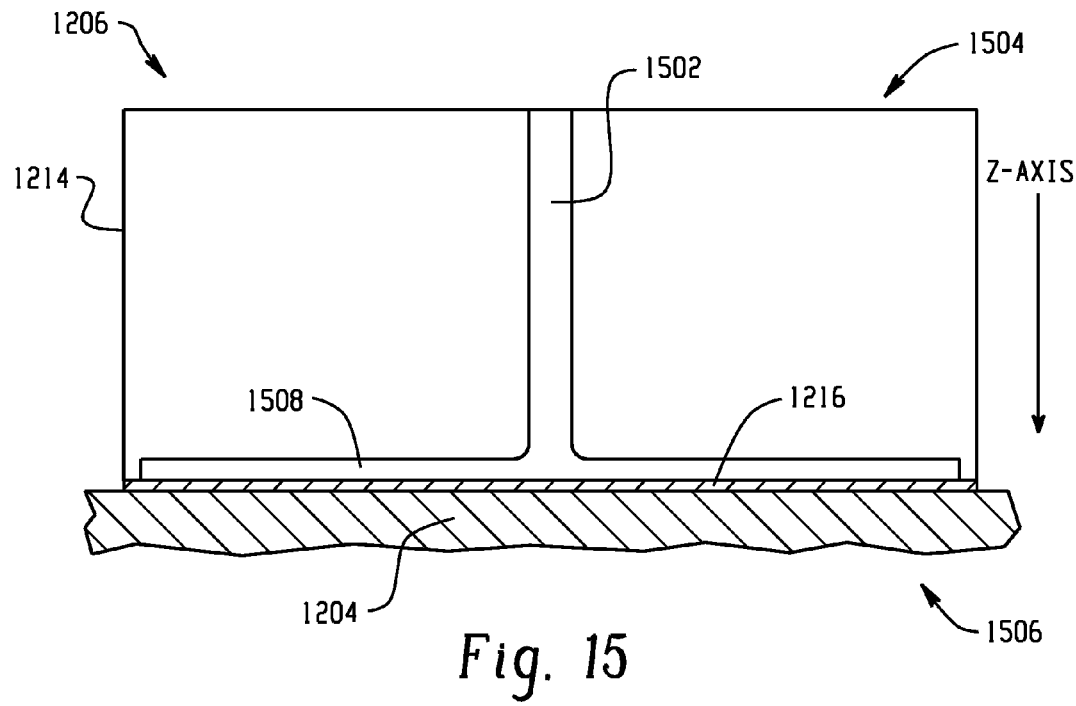
FIGS. 15-16 illustrate an example bearing block and brake pad.
Figure 16:
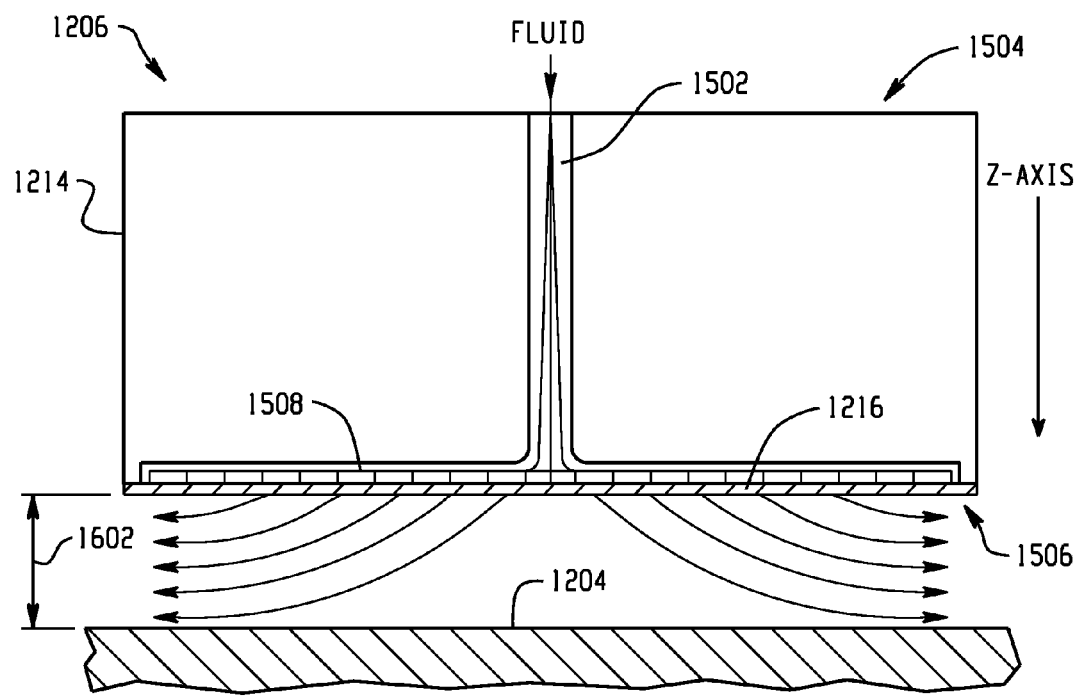

FIGS. 15 and 16 illustrate an example second portion 1206 with the brake pad 1216. In this example, a channel 1502 extends through the bearing block 1214 from a back side 1504 of the bearing block 1214 to a front side 1506 of the bearing block 1214 along the z-axis direction. The channel 1502 leads to a two-dimensional recess 1508 in the front 1506 of the bearing block 1214. The pad 1216 is affixed to the front 1506 of the bearing block 1214, covering the recess 1508. A suitable pad 1216 includes a relatively highly dense carbon material that is porous to air, has a relatively low wear rate, and can break the rotating gantry 106. Other pads are also contemplated herein.

As shown in FIG. 16, when the valve 1218 is closed, the fluid travels through the channel 1502 to the recess 1508, and disperses in a generally uniform manner through the porous material with respect to the race 1204, creating a gap 1602 between the pad 1216 and the race 1204. As shown in FIG. 15, when the valve 1218 is open, fluid does not flow through the valve 1218 to the bearing block 1214 and the pad 1216, and the pad 1216 engages the race 1204. The pores in the material generally are large enough so that debris does not clog the pores, and allowing air to pass through the pores and expel debris from the surface of the pad.

Figure 17:
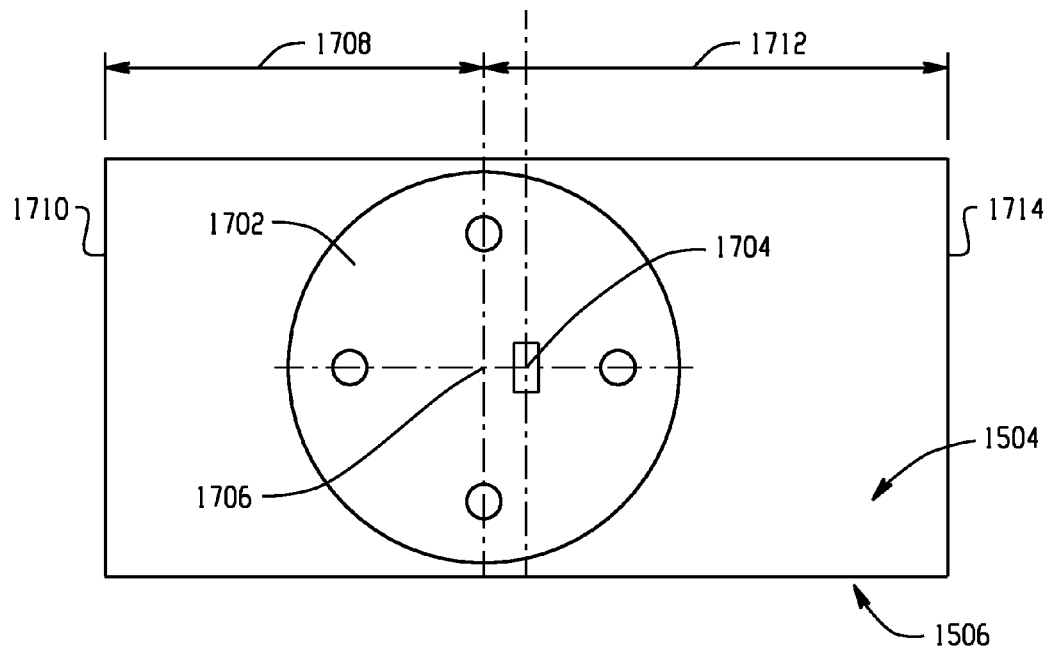
FIGS. 17-18 illustrate exemplary mounting of the bearing block.
Figure 18:
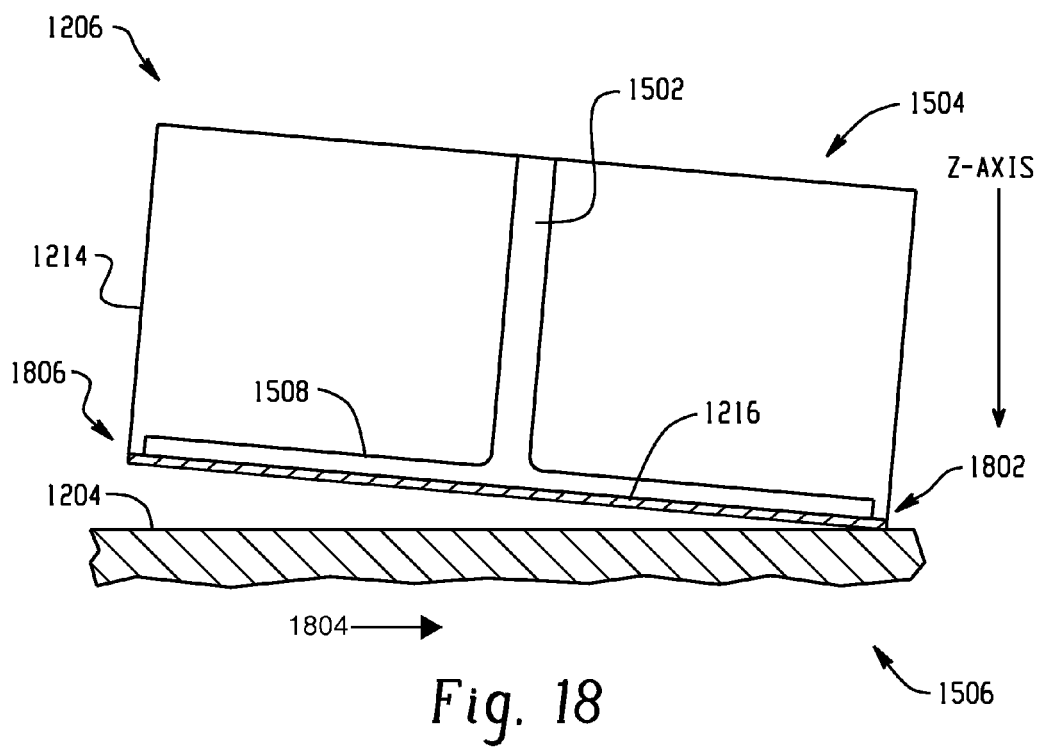

FIGS. 17 and 18 illustrate an example approach for mounting the second portion 1206 to the stationary gantry 102 using a mounting apparatus 1702. The mounting apparatus 1702 mounts the back side 1504 of the second portion 1206 to the stationary gantry 102. The illustrated mounting apparatus 1702 is configured to allow the second portion 1206 to translate along and/or rotate and is positioned offset from a center region 1704 of the second portion 1206 in the x-y plane.

As shown, a center region 1706 of the mounting apparatus 1702 is positioned at a first distance 1708 from a first 1710 of two ends of the second portion 1206 and at a second larger distance 1712 from a second 1714 of the two ends. As a result, the second portion 1206 tends to tilt as it translates away from the race 1204, with the shorter portion tilting towards the rotating gantry 106 and the longer portion tilting away from the rotating gantry 106.

Example tilting is shown in FIG. 18. Note that the second portion 1206 is mounted so that the shorter portion is a leading edge 1802, with respect to a rotational direction 1804 of the rotating gantry 106, and the longer portion is a trailing edge 1806, with respect to the rotational direction 1804 of the rotating gantry 106. The leading edge 1802 physically contacts the race 1204 before the trailing edge 1806 when the second portion 1206 engages the race 1204. This may mitigates gouging of the race 1204 by the second portion 1206, as may occur if the trailing edge 1806 were to contact the race 1204 first.

Although the illustrated embodiment describes use of a single second portion 1206 as a brake, it is to be appreciated that one or more of the second portions 1206 may include a block 1214 and a pad 1216 and be used as a brake. Where the system 100 includes a plurality of such second portions 1206, a sub-set or all of the second portions 1206 can be individually or concurrently used as the brake.

Moreover, the controller 114 may include intelligence that selects the particular second portion(s) 1206 to use as the brake. For example, in one instance the system 100 may select a second portions 1206 based on the wear of the pads 1216. In another instance, the system 100 may select a second portion(s) 1206 based on the rotational speed of the rotating gantry. For emergency purposes, in one embodiment, one or more of the second portions 1206 are automatically used to brake the rotating gantry 106 when power is lost.

In another embodiment, an orifice pad is used in addition to or in place of the air porous pad. Generally, an orifice pad uses one or more machined pockets that distribute air rather than pores. With one suitable orifice pad, the pockets are configured so that they do not become compromised by scratches or other defects. In one instance, sections of the pad that contact the race 1204 include a friction material. By configuring these sections so that they do not contact the orifices, the pad would behave substantially similar to a porous pad 1216 described herein.

In another embodiment, the bearing is a magnetic bearing. Generally, a magnetic bearing uses a magnetic force to create the air gap between the stationary and rotating sides. In one instance, the bearing is an electro-magnetic bearings powered by a supply that produces a magnetic force. By applying carbon to the bearing housing, a similar effect could be seen as describe herein. When power is removed from the electromagnetic bearing, the rotating portion would contact the carbon and slow to a stop. Note that in this case, merely removing the power actuates the brake.

Figure 19:
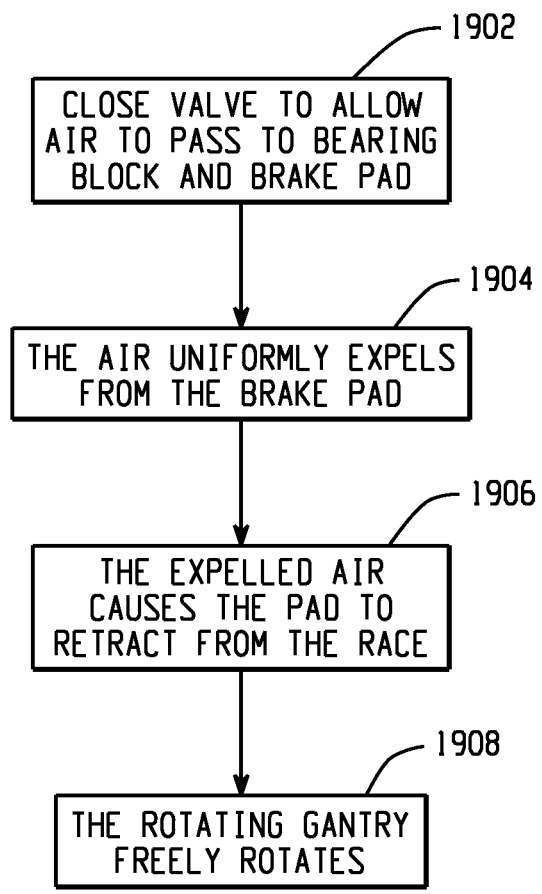
FIGS. 19-21 illustrate example methods.

FIG. 19 illustrates a method for employing a contactless bearing coupling the rotating gantry 106 to the stationary gantry 102 of the imaging system 100.

At 1902, the normally open valve 1218 is closed to allow air to pass from the air source 1222 to the channel 1502 of the bearing block 1214 of the second portion 1206.

At 1904, the air traverses the channel 1502 and expels in a generally uniform manner through the pad 1216 of the second portion 1206.

At 1906, the expelled air, which is directed at the race 1204 of the first portion 1202 of the bearing 1200, causes the second portion 1206 to retract away from the race 1204, leaving a frictionless gap therebetween.

At 1908, the rotating gantry 106 is driven to freely rotate with respect to the second portion 1206 of the bearing 1200.

Figure 20:
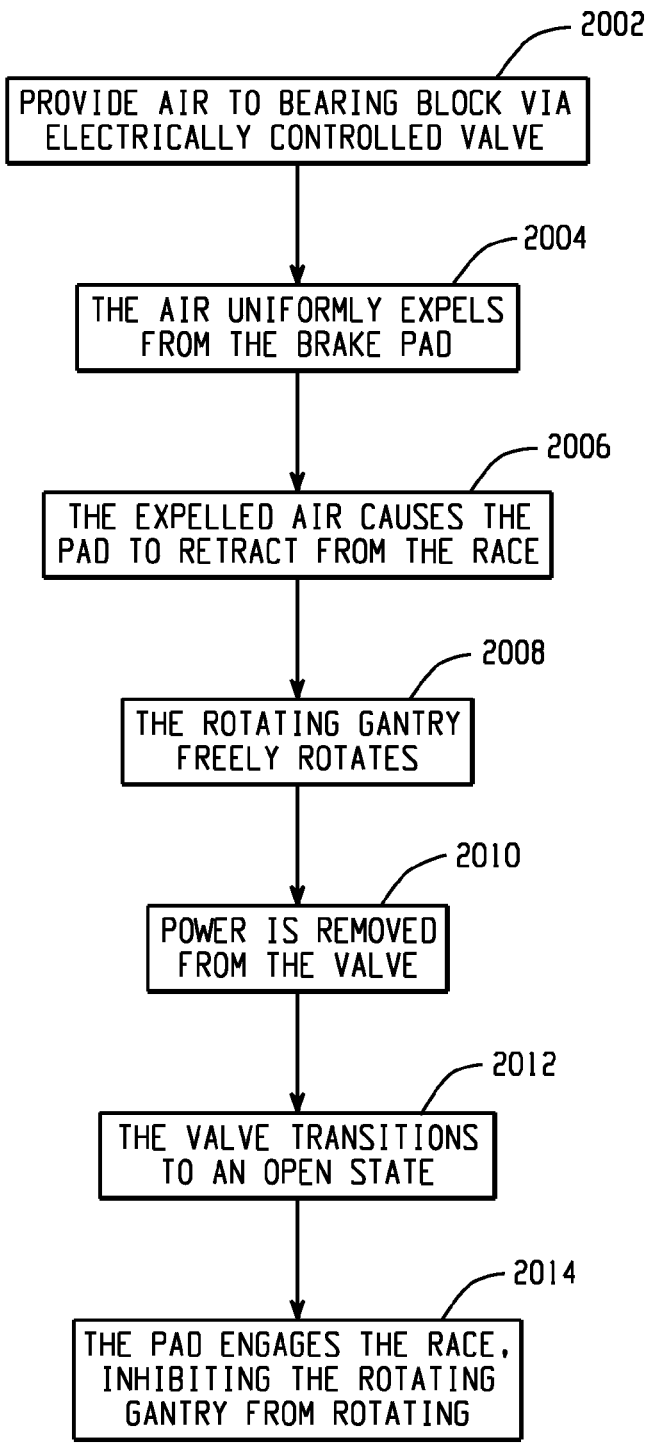

FIG. 20 illustrates a method for inhibiting or slowing down the rotating gantry 106 during loss of power.

At 2002, air is provided to the second portion 1206 through an electrically closed electrically controlled normally open valve, such as the valve 1218.

At 2004, the air traverses the channel 1502 and leaves the pad 1216 in a generally uniform manner.

At 2006, the air causes the second portion 1206 to retract away from the race 1204.

At 2008, the rotating gantry 106 is driven to freely rotate with respect to the second portion 1206 of the bearing 1200.

At 2010, when system power is lost, power is removed from the electrically controlled valve.

At 2012, the electrically controlled valve automatically opens, inhibiting air flow to the second portion 1206.

At 2014, the second section 1206 moves towards and engages the race 1204, inhibiting the rotating gantry 106 from rotating or holding the rotating gantry 106 at a static position.

Figure 21:
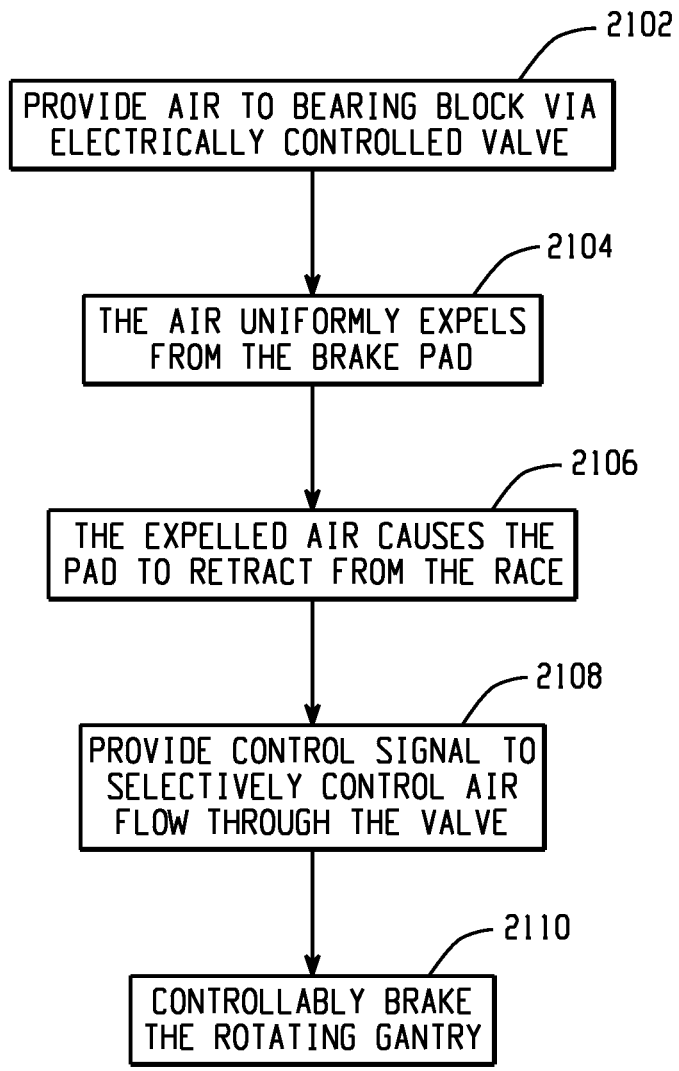

FIG. 21 illustrates a method for controllably inhibiting or slowing down the rotating gantry 106.

At 2102, air is provided to the second portion 1206 through an electrically closed electrically controlled normally open valve such as the valve 1218.

At 2104, the air traverses the channel 1502 and leaves the pad 1216 in a generally uniform manner, causing the second portion 1206 to retract away from the race 1204.

At 2106, the rotating gantry 106 is driven to freely rotate with respect to the second portion 1206 of the bearing 1200.

At 2108, a control signal is provided to the valve to selectively limit air flow therethrough.

At 2110, the pad 1216 controllably engages the race 1204, slowing down or stopping the rotating gantry 106 from rotating.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

The invention is claimed to be:

1. An imaging system, comprising:
   a rotating frame that rotates around an examination region about a z-axis;
   a second frame; and
   a support that rotatably couples the rotating frame to the second frame, wherein one of the rotating frame or the second frame is compliantly coupled to the support and the other of the rotating frame or the second frame is rigidly coupled to the support, the support comprises:
   a stator;
   a first bearing portion; and
   a bearing support that couples the stator and the first bearing portion, wherein the bearing support comprise: at least two members spaced apart from each other by a corresponding highly compliant region, wherein a first side of each member is coupled to the stator and a second side of each member is coupled to the first bearing portion.

2. The imaging system of claim 1, wherein the first bearing portion is compliantly coupled to the bearing support.

3. The imaging claim of claim 1, wherein the members deform under stress introduced via the imaging system, thereby reducing the stress.

4. The imaging system of claim 1, the rotating frame, comprising: a second bearing portion, wherein the rotating frame and the support are coupled through the first and second bearing portion.

5. The imaging system of claim 1, further including a frame stiffener that provides structural support for the rotating and second frames along transverse axes.

6. The imaging system of claim 1, further including a braking component that selectively applies a brake to the rotating frame.

7. The imaging system of claim 6, the braking component, comprising:
an actuator with a brake shoe, wherein the actuator urges the brake shoe towards the rotating frame to brake the rotating frame.

8. The imaging system of claim 6, wherein the breaking component is part of a contactless fluid bearing that includes a first portion affixed to the rotating frame; and a second portion affixed to the second frame, wherein the second portion engages the first portion to brake the rotating frame.

9. The imaging system of claim 8, wherein the breaking component is controlled by an electrically controlled normally open valve, and the valve automatically opens when power is removed from the system, thereby braking the rotating frame.

10. An imaging system, comprising:
a rotating frame that rotates around an examination region about a z-axis;
a tilt frame that tilts along the z-axis, wherein the rotating frame is rotatably coupled to the tilt frame;
a stationary frame, wherein the tilt frame is tiltably coupled to the stationary frame; and
a frame stiffener that provides structural support for the rotating and tilt frames along transverse axes, the frame stiffener, comprising:
a first portion affixed to the stationary frame and including at least one guide that form a channel; and
a second protruding portion affixed to the tilt frame; wherein the second protruding portion is guided in the channel by the at least one guide.

11. The imaging system of claim 10, the first portion, comprising:
a first stationary side; and
a second free floating side, wherein the first and second sides are separated from each other by a highly compliant region and coupled together at a base.

12. The imaging system of claim 11, further comprising:
a preloaded fastener that urges the second free floating side towards the first stationary side.

13. The imaging system of claim 12, wherein the urged second free floating side physically engages the second protruding portion when the second protruding portion is in the channel.

14. The imaging system of claim 13, wherein the second free floating side laterally supports the second protruding portion, thereby laterally supporting the tilt frame.

15. The imaging system of claim 10, further including at least a one frame stiffener, wherein the frame stiffeners are located such that at least one frame stiffener is within at least one of the corresponding channels for all tilt angles.

16. An imaging system, comprising:
a rotating gantry that rotates around an examination region about a z-axis;
a stationary gantry;
a contactless fluid bearing that rotably couples the rotating gantry and the stationary gantry, the contactless bearing including:
a first portion affixed to the rotating gantry; and
a second portion affixed to the stationary gantry, wherein the second portion engages the first portion to brake the rotating gantry.

17. The imaging system of claim 16, further comprising:
a valve that supplies air to the second portion, wherein the second portion retracts away from the first portion in response to air being supplied to the second portion by the valve, allowing the second portion and hence the rotating gantry to feely rotate.

18. The imaging system of claim 17, wherein the second portion physically engages the first portion when air is not supplied to the second portion by the valve, inhibiting or slowing down a rotating second portion and hence a rotating, rotating gantry.

19. The imaging system of claim 16, wherein the valve is an electrically controlled normally open valve, and the valve automatically opens when power is removed from the system, thereby braking the rotating gantry.

20. The imaging system of claim 16, wherein the valve is an electrically controlled normally open valve, and the valve is selectively opened and closed based on a control signal.

21. The imaging system of claim 16, the second portion, comprising:
a bearing block with a channel; and
a brake pad affixed to the bearing block,
wherein air flowing through the channel expels out of the brake pad and forms a frictionless air gap between the brake pad and the second portion.

22. The imaging system of claim 16, the second portion, comprising: a
first end;
a second opposing end; and
a mounting apparatus that mounts the second portion to the stationary gantry, wherein the mounting apparatus is located offset from a center region of the second portion with respect to the first and second ends.

23. The imaging system of claim 22, wherein the second portion tilts about the z-axis such that the end further away from the center is closer to the second portion relative to the other end.

24. The imaging system of claim 22, wherein the end further away from the center is a leading edge and the other end is a trailing, with respect to a rotational direction of the second portion.

25. A method, comprising:
rotatably coupling a rotating frame of an imaging system and a second frame of the imaging system, wherein one of the rotating frame or the second frame of the imaging system is compliantly coupled to a support of the imaging system and the other of the rotating frame or the second frame of the imaging system is rigidly coupled to the support of the imaging system, wherein the support comprises: a stator; a first bearing portion: and a bearing support that couples the stator and the first bearing portion, wherein the bearing support comprise: at least two members spaced apart from each other by a corresponding highly compliant region, wherein a first side of each member is coupled to the stator and a second side of each member is coupled to the first bearing portion.

26. A method, comprising: providing lateral support for rotating and tilt frames of an imaging system via a frame stiffener, wherein the tilt frame is tiltably coupled to a stationary frame of the imaging system and tilts along a z-axis and the rotating frame is rotatably coupled to the tilt frame and rotates about the z-axis, and the frame stiffener includes a first portion affixed to the stationary frame and including at least one guide that form a channel; and a second protruding portion affixed to the tilt frame; wherein the second protruding portion is guided in the channel by the at least one guide.

27. A method, comprising: employing a first portion of a contactless bearing of an imaging system to brake a rotating second portion of the contactless bearing and hence a rotating gantry coupled to the second portion, wherein the contactless bearing couples a rotating gantry of the imaging system to a stationary gantry of the imaging system.

28. The method of claim 27, wherein the first portion includes a first end and a second opposing end and the first portion mounts to the stationary gantry such that it is located offset from a center region of the first portion with respect to the first and second ends, the center is closer to the second portion relative to the other end.

\* \* \* \* \*